US009795648B2

(12) United States Patent
Yan et al.

(10) Patent No.: US 9,795,648 B2
(45) Date of Patent: Oct. 24, 2017

(54) PHARMACEUTICAL COMPOSITION FOR TREATING HEADACHE, AND PREPARATION METHOD THEREOF

(71) Applicant: Tasly Pharmaceutical Group Co., Ltd., Tianjin (CN)

(72) Inventors: Xijun Yan, Tianjin (CN); Naifeng Wu, Tianjin (CN); Shunnan Zhang, Tianjin (CN); Jianhui Yang, Tianjin (CN); Yan Liu, Tianjin (CN); Xingyun Shao, Tianjin (CN); Song Gao, Tianjin (CN); Lina Dong, Tianjin (CN); Xiaolin Bai, Tianjin (CN); Yan Sun, Tianjin (CN); Bo Xu, Tianjin (CN); Yongfeng Zheng, Tianjin (CN); Lijun Fan, Tianjin (CN)

(73) Assignee: Tasly Pharmaceutical Group Co., Ltd., Tianjin (CN)

( * ) Notice: Subject to any disclaimer, the term of this patent is extended or adjusted under 35 U.S.C. 154(b) by 70 days.

(21) Appl. No.: 14/654,151

(22) PCT Filed: Dec. 19, 2013

(86) PCT No.: PCT/CN2013/089960
§ 371 (c)(1),
(2) Date: Jun. 19, 2015

(87) PCT Pub. No.: WO2014/094632
PCT Pub. Date: Jun. 26, 2014

(65) Prior Publication Data
US 2015/0352168 A1  Dec. 10, 2015

(30) Foreign Application Priority Data

Dec. 21, 2012 (CN) .......................... 2012 1 0562103

(51) Int. Cl.
*A61K 36/00* (2006.01)
*A61K 36/74* (2006.01)
*A61K 36/66* (2006.01)
*A61K 36/268* (2006.01)
*A61K 36/804* (2006.01)
*A61K 36/482* (2006.01)
*A61K 36/536* (2006.01)
*A61K 36/9068* (2006.01)
*A61K 35/618* (2015.01)
*A61K 36/232* (2006.01)
*A61K 36/48* (2006.01)
*A61K 36/505* (2006.01)
*A61K 36/65* (2006.01)
*A61K 36/236* (2006.01)
*A61K 36/486* (2006.01)
*A61K 36/71* (2006.01)
*A61K 9/16* (2006.01)

(52) U.S. Cl.
CPC ............ *A61K 36/74* (2013.01); *A61K 9/1623* (2013.01); *A61K 9/1652* (2013.01); *A61K 35/618* (2013.01); *A61K 36/232* (2013.01); *A61K 36/236* (2013.01); *A61K 36/268* (2013.01); *A61K 36/48* (2013.01); *A61K 36/482* (2013.01); *A61K 36/486* (2013.01); *A61K 36/505* (2013.01); *A61K 36/536* (2013.01); *A61K 36/65* (2013.01); *A61K 36/66* (2013.01); *A61K 36/71* (2013.01); *A61K 36/804* (2013.01); *A61K 36/9068* (2013.01); *A61K 2236/00* (2013.01)

(58) Field of Classification Search
None
See application file for complete search history.

(56) References Cited

FOREIGN PATENT DOCUMENTS

| CN | 1073874 A | * | 7/1993 |
|---|---|---|---|
| CN | 1714839 A | | 1/2006 |
| CN | 1857400 A | | 11/2006 |
| CN | 1872217 A | | 12/2006 |
| CN | 1872219 A | | 12/2006 |
| CN | 1919272 A | | 2/2007 |
| CN | 1919273 A | | 2/2007 |
| CN | 101053607 A | | 10/2007 |
| CN | 101129503 A | | 2/2008 |
| CN | 101156935 A | | 4/2008 |
| CN | 101194958 A | | 6/2008 |
| CN | 101194959 A | | 6/2008 |
| CN | 101428091 A | | 5/2009 |
| CN | 101439063 A | | 5/2009 |
| CN | 102698030 A | | 10/2012 |
| CN | 102716256 A | | 10/2012 |
| CN | 102727858 A | | 10/2012 |
| EP | 1 930 020 A1 | | 6/2008 |
| JP | 2009505991 A | | 2/2009 |

OTHER PUBLICATIONS

Written Opinion of the International Search Authority for parent PCT/CN2013/089960 application (dated Jun. 21, 2015).
International Search Report for parent PCT/CN2013/089960 application (dated Jun. 26, 2014).
Cheong, Byung-Shik, et al., "Modulation of Corydalis tuber on Glycine-Induced Ion Current in Acutely Dissociated Rat Periaqueductal Gray Neurons", Korean Journal of Oriental Medicine, 2003, vol. 24(4), pp. 34-42.
He, Qing-yong, et al., "Thirty-two Cases of Vascular Headache Treated by Acupuncture Combined with Chinese Herbal Decoction", Journal of Traditional Chinese Medicine, Dec. 2009, vol. 29(4), pp. 253-257.
Xu, Xiang-Shun, et al., "The Antioxidant Cerebralcare Granule Attenuates Cerebral Microcirculatory Disturbance During Ischemia-Reperfusion Injury", Shock, 2009, vol. 32(2), pp. 201-209.

(Continued)

*Primary Examiner* — Qiuwen Mi
(74) *Attorney, Agent, or Firm* — McDonnell Boehnen Hulbert & Berghoff LLP

(57) ABSTRACT

A pharmaceutical composition for treating headache, prepared from eleven Chinese herbal medicines: Chinese angelica root, *ligusticum chuanxiong*, *radix paeoniae lactiflorae*, prepared rhizome of rehmannia, uncaria tomentosa, leatherleaf milletia, prunella vulgaris, sicklesenna seed, pearl shell, *corydalis* tuber, and *asarum*, and a proper amount of adjuvant materials. A preparation method of the pharmaceutical composition, and uses thereof in the preparation of drugs for treating various headaches, traumatic cranial nerve syndrome, dizziness and vertigo, vexation and irritability, insomnia and dreaminess.

13 Claims, No Drawings

OTHER PUBLICATIONS

Yao, Gang, et al., "Effects of Toutongning Capsule on Enkephalin Expression in a Rat Migraine Headache Model", Neural Regeneration Research, Mar. 2011, vol. 6(9), pp. 661-665.

Yul, Kim Seung, "Clinical Application of Oriental Medicine Hyungbangjihwangtang", J. of Const. Med., 1996, vol. 8(1) pp. 413-416.

Office Action of the corresponding Chilean Application No. PCT/2015-001772 dated Jun. 19, 2015, received from the National Institute of Industrial Property (INAPI), pp. 1-13.

Meng, Bin, et al. "Fingerprint Comparison of the Extraction of Rhizoma Coptidis and Cortex Magnoliae Officinalis Extracted by Ethanol Together and Single", Chin JMAP, Sep. 2009, vol. 26(9), pp. 734-736.

Traditional Medicine Chemistry, 2003, pp. 1-5.

\* cited by examiner

PHARMACEUTICAL COMPOSITION FOR TREATING HEADACHE, AND PREPARATION METHOD THEREOF

This application is a national stage application under 35 U.S.C. §371 of International Application No. PCT/CN2013/089960, filed on Dec. 19, 2013, which claims priority to Chinese Patent Application No. 201210562103.8, filed Dec. 21, 2012, both of which are incorporated by reference herein in their entirety.

FIELD OF THE INVENTION

The present invention relates to the field of Traditional Chinese medicine (TCM). More specifically, the invention relates to pharmaceutical composition for treating headache, preparative method and its use thereof.

BACKGROUND OF THE INVENTION

Headache is a common symptom in daily life. Almost everyone will have headache in lifetime. The causes of headache are varied. By now, there are a lot of drugs for treating headache abroad or in China, most of which, however, focus on symptomatic treatment of stopping ache (in very few cases, headache is treated by surgery). The results are not satisfactory, because the drugs focus on symptomatic treatment rather than root cause. As a result of this, headache attacks patients recurrently. Long-term use of analgesic agents may cause drug resistance and addiction, so the drug of this kind should not be used for long time. Yet, the headache cannot be cured radically. Besides, according to conditions with different causes, there are different sorts of drugs applied clinically, e.g. the anti-anxiety agent, antidepressant agent, sympathetic inhibitor, calcium channel blockers and antiepileptic agents etc. Due to their severe side effects, long-term administration will make their efficacy reduced so much that the patients have to increase dose of drug gradually. The result, however, is not satisfactory. The more drugs they take, the severer the headache is. Now, Zhengtian pill (Zhengtianwan) is a Traditional Chinese medicine (TCM) whose formula comprises both TCM and chemical drug. The TCM works by a mechanism of activating blood by removing stasis and the chemical drug stopping pain. In practice, its curative effect is not definite to achieve the purpose of curing radically. Now, there are a lot of TCMs for treating headache. But most of them take effect more slowly; and this drawback will influence life quality of the patients.

Chinese Patent (No. ZL 93100050.5) disclosed a medicinal composition comprising 11 TCMs of *Radix Angelicae Sinensis* (Dang gui) and *Rhizoma Chuanxiong* (Chuan xiong), *Radix Paeoniae alba* (Bai shao), *Radix Rehmanniae Preparata* (Shu dihuang), *Ramulus Uncariae cum Uncis* (Gou teng), *Caulis Spatholobi* (Ji Xueteng), *Spica Prunellae* (Xia Kucao), *Semen Cassiae* (Jue mingzi), *Concha Margaritifera Usta* (Zhen zhumu), *Rhizoma Corydalis* (Yuan hu) and *Asarum herb* (Xi xin). It is the fruits of long-term clinical practice under the guidance of Chinese medicine theory, having the therapeutic effects of treating headache caused by inner damage. Clinically, it can be applied to treat several headache diseases, such as the angioneurotic headache, migraine, and some symptoms like dizziness and headache etc. caused by hypertension. According to the proportion of this recipe, the granule of this composition is produced by Tasly Pharmaceutical Group Co. Ltd., named as "Yang Xue Qing Nao Granule". The functions and indications approved by the authorities are nourishing blood and calming liver, activating blood and removing obstruction in channels, used for diverse types of headache elicited by blood deficiency and hyperactivity of liver, traumatic cranial nerve syndrome, dizziness and vertigo, vexation and irritation, insomnia and dreaminess. In clinic, it has been usually used for treatment headache caused by blood deficiency, blood stasis, and deficiency of Yin and hyperactivity of Yang. Since coming into the market, Yang Xue Qing Nao Granule has gained wide popularity among the patients due to its reassured therapeutic effects.

Now, it has been literally reported that the Yang Xue Qing Nao Granule is usually prepared by the following method. The 11 TCMs are extracted with water, which is precipitated with ethanol to give the extract, and then the extract is mixed with excipients to prepare into various kinds of pharmaceutical formulations. For example, Chinese patents (No. 03140844.3, 200410019825.4) disclosed a process that the 11 TCMs were mixed in proportion, extracted with water for 3 times, combined to get an extract after appropriate concentration, which was added with 2 fold of ethanol to leave it to stand still for 24 hours to precipitate to get supernatant. The supernatant was concentrated to an extract with relative density of 1.3~1.4. The yield rate was 10%. Aforesaid extract was mixed with sucrose and dextrin in a proportion of 1:3:1 to make granule.

However, due to the different nature of each TCM, the extraction of active ingredients by using method of extracting all together usually results in the extraction incomplete or raises the defect of low yield rate. For example, main ingredients of *Radix Angelicae Sinensis* (Dang gui) and *Rhizoma Chuanxiong* (Chuan xiong) are ethanol soluble, so the ethanol was better. In the same manner, the *Ramulus Uncariae cum Uncis* contains a variety of indole alkaloids, which is dominated by rhynchophylline and isorhynchophylline and a small amount of flavone constituents. Its water decoction and extract are proved to have significantly bioactive effects of sedation, analgesia and antihypertension. Thus, the extraction by water is a more suitable.

As shown in Chinese patents (200510073290.3 and 200510014828.3), 11 TCMs were disclosed, in which *Radix Angelicae Sinensis, Rhizoma Chuanxiong, Radix Paeoniae alba* and *Rhizoma Corydalis* were refluxed with ethanol to have a refluxing solution, the residue was mixed with the other 6 TCMs (excluding *Ramulus Uncariae cum Uncis*) including *Radix Rehmanniae Preparata* etc. and extracted with water for 3 times. During the process of $3^{rd}$ decoction, the *Ramulus Uncariae cum Uncis* was added, and the extraction liquid was combined to concentrate in vacuum. Ethanol was used to precipitate and the obtained solution was left standing still. After being filtered, the filtrate was mixed with aforesaid refluxing solution, and ethanol was recovered under reduced pressure, concentrated and dried to obtain the extract.

In practice, however, extracting *Radix Paeoniae alba* combined with other TCMs will result in the final extract somewhat less in melting ability. Later addition of the *Ramulus Uncariae cum Uncis* into the extract may get the medicine float on the surface, so as to influence the extraction. Not only that, but the operation is complicated with the risk of dangerous steam. Extraction of *Semen Cassiae* by water is prone to cause problems of paste extracting tank or difficult draining.

In view of aforesaid problems, after repeated experimental researches, a new preparation method and a medicinal composition made by this new method have been developed.

DETAILED DESCRIPTION OF THE INVENTION

The objective of present invention is to provide a pharmaceutical composition for treating headache.

Another objective of present invention is to provide a preparing method of said composition.

Another objective of present invention is to provide a use of said composition in preparation of drugs for treating headache, traumatic cranial nerve syndrome, dizziness and vertigo, vexation and irritability, insomnia and dreaminess.

The composition of present invention comprises: 4-9 weight parts of *Radix Angelicae Sinensis*, 4-9 weight parts of *Rhizoma Chuanxiong*, 2-8 weight parts of *Radix Paeoniae alba*, 2-8 weight parts of *Radix Rehmanniae Preparata*, 10-15 weight parts of *Ramulus Uncariae cum Uncis*, 10-15 weight parts of *Caulis Spatholobi*, 10-15 weight parts of *Spica Prunellae*, 10-15 weight parts of *Semen Cassiae*, 10-15 weight parts of *Concha Margaritifera Usta*, 4-9 weight parts of *Rhizoma Corydalis* and 0.5-2 weight parts of *Herba Asari*. Said composition is prepared by a method as follows:

a). Preparation of #1 Extract: *Radix Angelicae Sinensis*, *Rhizoma Chuanxiong*, *Rhizoma Corydalis* and *Semen Cassiae* are mixed, extracted by using heating refluxing with ethanol, and filtered to remove impurities; and the ethanol is recovered and concentrated to give #1 Extract for later use;

b). Preparation of #2 Extract: *Radix Paeoniae alba* is extracted by using heating refluxing with ethanol, and filtered; and the ethanol is recovered and concentrated to give #2 Extract for later use;

c). Preparation of #3 Extract: *Radix Rehmanniae Preparata*, *Ramulus Uncariae cum Uncis*, *Caulis Spatholobi*, *Spica Prunellae*, *Concha Margaritifera Usta* and *Herba Asari* are mixed, decocted with water, filtered, concentrated, into which ethanol is added to leave it to stand still, and filtered; and the ethanol is recovered and concentrated to give #3 Extract for later use;

d). Preparation of formulations: aforesaid three Extracts are added with appropriate amount of excipients, dried and granulated to obtain the final product.

Preferably, said composition of present invention is prepared by a method as follows:

a). Preparation of #1 Extract: *Radix Angelicae Sinensis*, *Rhizoma Chuanxiong*, *Rhizoma Corydalis* and *Semen Cassiae* are mixed, extracted by using heating refluxing with 3~6 fold of 50~80% ethanol for 2~3 times, the first time for 0.5~2.5 hours; the second and/or third time for 0.5~2 hours, and filtered to remove the impurities; and the ethanol is recovered and concentrated until the relative density is 1.250~1.350 (70~80° C.) to give #1 Extract for later use;

b). Preparation of #2 Extract: *Radix Paeoniae alba* is added with 3~6 fold of 50~80% ethanol, soaked, extracted by using heating refluxing for 2~3 times, the first time for 0.5~2.5 hours, the second and/or third time for 0.5~2 hours, and filtered; and the ethanol is recovered and concentrated until the relative density is 1.10~1.35 (55~65° C.) to give #2 Extract for later use;

c). Preparation of #3 Extract: *Radix Rehmanniae Preparata*, *Ramulus Uncariae cum Uncis*, *Caulis Spatholobi*, *Spica Prunellae*, *Concha Margaritifera Usta* and *Herba Asari* are combined, decocted with 4~10 fold of water for 2~3 times, the first time for 0.5~3 hours, the second and/or third time for 1~3 hours, filtered, concentrated until the relative density is 1.06~1.10 (75~85° C.), into which ethanol is added to make a final ethanol content of 60~85%, left to stand still for 12~24 hours, and filtered; and the ethanol is recovered and concentrated until the relative density is 1.270~1.350 (75~85° C.) to give #3 Extract for later use;

d). Preparation of formulations: aforesaid three Extracts are added with appropriate amount of excipients, dried, granulated to obtain the final product.

More preferably, said composition of present invention is prepared by a method as follows:

a). Preparation of #1 Extract: *Radix Angelicae Sinensis*, *Rhizoma Chuanxiong*, *Rhizoma Corydalis* and *Semen Cassiae* are mixed, extracted by using heating refluxing for 2 times with 4 fold of 70% ethanol, the first time for 2 hours and the second time for 1 hour, and filtered to remove the impurities; and the ethanol is recovered and concentrated until the relative density is 1.300~1.310 (74~76° C.) to give #1 Extract for later use;

b). Preparation of #2 Extract: *Radix Paeoniae alba* is added with 4 fold of 60% ethanol, soaked, extracted by using heating refluxing for 2 times, the first time for 2 hours and the second time for 1 hour, and filtered; and the ethanol is recovered and concentrated until the relative density is 1.23~1.33 (65° C.) to give #2 Extract for later use;

c). Preparation of #3 Extract: *Radix Rehmanniae Preparata*, *Ramulus Uncariae cum Uncis*, *Caulis Spatholobi*, *Spica Prunellae*, *Concha Margaritifera Usta* and *Herba Asari* are mixed, decocted for 2 times with 5 fold of water, the first time for 2 hours and the second time for 1 hour, filtered, concentrated until the relative density is 1.06~1.10 (80° C.), into which ethanol is added to make a final ethanol content of 65~70%, left to stand still for 12~24 hours, and filtered; and the ethanol is recovered and concentrated until the relative density is 1.320~1.325 (79~81° C.) to give #3 Extract for later use;

d). Preparation of formulations: aforesaid three Extracts are added with appropriate amount of excipients, dried, granulated to obtain the final product.

Wherein, said excipients in step d) include one or more kinds of filling agent and flavoring agent.

Said filling agent is selected from one or more kinds of cellulose, starch, soluble starch, sugar powder, dextrin, mannitol, sucrose, lactose and microcrystalline cellulose, etc.

Said flavoring agent is selected from one or more kinds of steviosin, aspartame, glycerol, saccharin sodium, sorbitol, mannitol, xylitol, high fructose and sodium cyclamate.

Preferably, said filling agent is selected from dextrin, starch, soluble starch, sucrose, lactose and microcrystalline cellulose, and said flavoring agent is selected from steviosin and aspartame.

Most preferably, said filling agent is selected from dextrin and flavoring agent is selected from steviosin.

In one embodiment, the ratio of aforesaid three Extracts prepared by *Radix Angelicae Sinensis*, *Rhizoma Chuanxiong*, *Radix Paeoniae alba*, *Radix Rehmanniae Preparata*, *Ramulus Uncariae cum Uncis*, *Caulis Spatholobi*, *Spica Prunellae*, *Semen Cassiae*, *Concha Margaritifera Usta*, *Rhizoma Corydalis* and *Herba Asari* to the excipients is 40:60 to 65:35 by weight percentage.

In another embodiment, the ratio of aforesaid three Extracts prepared by *Radix Angelicae Sinensis*, *Rhizoma Chuanxiong*, *Radix Paeoniae alba*, *Radix Rehmanniae Preparata*, *Ramulus Uncariae cum Uncis*, *Caulis Spatholobi*, *Spica Prunellae*, *Semen Cassiae*, *Concha Margaritifera Usta*, *Rhizoma Corydalis* and *Herba Asari* to the excipients is 55:45 to 65:35 by weight percentage.

Wherein, aforesaid ratio is a ratio of the dried extractum converted from aforesaid three Extracts to the excipients.

According to present invention, said pharmaceutical composition can be prepared into any one of pharmaceutically acceptable oral formulations, including, but not limited to, granules, tablets and capsules, etc, preferably the granules.

According to present invention, said formulation may be prepared by any one of pharmaceutically acceptable methods, e.g. spray drying granulation method, fluidized-bed spray granulation method, wetting granulation method, dry granulation method and rolling granulation method.

Preferably, said formulation may be prepared by the fluidized-bed spray granulation method.

According to present invention, said fluidized-bed spray granulation method comprises following steps: taking a part of filling agent, dissolving it with purified water, adding flavoring agent to dissolve by well-stirring to give slurry; adding well-prepared three Extracts into aforesaid slurry stepwise, stirring, adjusting density of the slurry, online filtering; putting the rest of filling agent into a granulator; performing spray granulation by adjusting granulating parameters; drying; granulating with a sieve; mixing totally and packaging to have the final product.

Wherein, the addition amount of said flavoring agent accounts for 0~1% by weight of the total filling agent. The ratio between the part of filling agent firstly added and the rest of the filling agent is 1:4 to 1.5:1 by weight percentage.

According to present invention, said pharmaceutical composition may be prepared into appropriate package specification, which depends on its various dosage forms, e.g. for the granules, the specification can be selected from 3 g/bag or 4 g/bag.

According to Present Invention, Extracting Method of Said Pharmaceutical Composition is Obtained by Following Screening Experiments.

1. the Reason why to Extract 11 TCMs Respectively

The main ingredients of *Radix Angelicae Sinensis* include: ferulic acid, capable of inhibiting blood coagulation and thrombus formation; water-soluble vitamin $B_{12}$, folic acid, folinic acid and nicotinic acid, capable of promoting generation of erythrocyte and hemoglobin significantly; and angelica polysaccharide, capable of facilitating growth of WBC reticular cell in mice and resisting anemia.

The main ingredients of *Rhizoma Chuanxiong* include special smell volatile oil-like alkaloids, ferulic acid and volatile oil, etc. The alcohol extract of the *Rhizoma Chuanxiong* has effects of dilating coronary artery, increasing coronary blood flow, protecting myocardium against ischemia, reducing blood pressure significantly, anticoagulation and anti-thrombus, etc. Besides, the tetramethylpyrazine therein is capable of sedation, dilating blood vascular, protecting myocardium against ischemia, as well as reducing blood pressure, anticoagulation and anti-thrombus, etc. The main bioactive ingredients are ethanol soluble in both *Rhizoma Chuanxiong* and *Radix Angelicae Sinensis*, so ethanol extraction is used.

*Radix Paeoniae alba* mainly contains a number of glycosides such as paeoniflorin, as well as volatile oil, tannins and sugar. Its total glycosides are proven to have effects of anti-inflammation, immune regulation, protecting liver, sedation and analgesia, etc. Among them, the paeoniflorin is at the highest concentration, which is easily extracted with ethanol or hot water due to its ester structure. As a result, the extract by ethanol solution is more stable.

The main ingredients of *Rhizoma Corydalis* are numerous alkaloids, among which the tetrahydropalmatine, corydaline, corydalis L and dehydrocorydaline are proven to have the stronger biological functions, capable of significantly sedating, hypnotizing, reducing coronary resistance and increasing blood flow, etc. All of *Rhizoma Corydalis*' ethanol extract, vinegar extract and water extract are found to have effect of relieving pain, and the ethanol one has the best effect among others. At the same time, they have certain of central sedation effect. Its alkaloid is mainly composed of quarternary amine alkali and tertiary amine alkali; the former is water soluble and extracted with water. Both, however, can be extracted with ethanol solution and the yield rate is high.

*Semen Cassiae* contains a series of ingredients of physcion, chrysophanol, emodin, rhein and *Semen Cassiae* lactone. Thus, extraction-by-ethanol is reasonable.

*Ramulus Uncariae cum Uncis* mainly contains various types of indole alkaloids, dominated by rhynchophylline and isorhynchophylline, as well as a little flavonoid. Both its water decoction and extract have marked effects of sedation, relieving pain and reducing blood pressure. Therefore, extraction-by-water is reasonable.

For the rest in this pharmaceutical composition, *Radix Rehmanniae Preparata, Caulis Spatholobi, Spica Prunellae, Concha Margaritifera Usta* and *Herba Asari* work as adjuvant drugs and courier drugs in this formula. The chemical ingredients contained therein include alcohols, amino acids, sterols, anthraquinones, many kinds of sugars and a variety of essential trace elements such as Fe. The water decoction thereof is found to have blood-enriching effect of increasing RBC count, having hemoglobin increased, reducing blood sugar, reducing blood pressure and lowering blood lipid, etc. As a result, according to the requirements of formula and quality of bioactive ingredients, the water-extracting-alcohol-precipitating method is used to extract the bioactive ingredients.

On the basis of aforesaid analysis, the extraction-by-ethanol method is applied to the medicines of *Radix Angelicae Sinensis, Rhizoma Chuanxiong, Radix Paeoniae alba, Rhizoma Corydalis* and *Semen Cassiae*; the water-extracting-alcohol-precipitating method to *Radix Rehmanniae Preparata, Caulis Spatholobi, Spica Prunellae, Concha Margaritifera Usta* and *Herba Asari*.

2. Investigation of Extracting *Radix Paeoniae Alba* Alone or in Combination

*Radix Paeoniae alba* is the main drug in the formula, whose main bioactive ingredient, paeoniflorin, acts as a determination indicator. The yield rate, paeoniflorin content and dissolvability were used as the indicators for investigation of extracting *Radix Paeoniae alba* alone or in combination. Production processes were designed respectively, wherein the $1^{st}$ process included the steps of taking *Radix Paeoniae alba* at prescription dose, into which 5 fold of 70% ethanol was added to extract by refluxing twice, 2 hours for each time; and the $2^{nd}$ process included the steps of taking *Radix Paeoniae alba, Radix Angelicae Sinensis, Rhizoma Chuanxiong, Rhizoma Corydalis* and *Semen Cassiae* at prescription dose, into which 5 fold of 70% ethanol was added to extract by refluxing twice, 2 hours for each time. Resultant extracts were combined respectively, appropriate quantity of the extracts (approximately equal to 0.03 g crude medicine of *Radix Paeoniae alba*) were sucked, ethanol was added to a constant volume of 20 ml, and filtered to get the liquid as the sample solution. The rest of the extracts was dried to investigate their yield rate, paeoniflorin content and dissolvability.

Method for Determination of Paeoniflorin

Apparatus and Reagent

Agilent 1100 HPLC was equipped with quaternary pump, DAD, automatic sampler, online degasser and column thermostat.

Standard paeoniflorin (obtained from China Pharmaceutical Biological Products Analysis Institute), methanol (chromatographically pure), purified water, isopropanol, citric acid (analytically pure)

Chromatographic conditions: Agilent Zorbax SB-$C_{18}$ column (250 mm×4.6 mm, 5 μm)

Mobile phase: isopropanol-methanol-5% citric acid solution (2:18:80)

Flow rate: 1.0 ml/min; column temperature: 30° C.; detection wavelength: 240 nm

Preparation of testing solution: as mentioned before.

Preparation of standard solution: appropriate quantity of standard paeoniflorin was taken and weighed accurately to prepare the standard solution (with 1 ml solution containing 0.015 mg solute) by adding 80% methanol.

Measuring method: 10 ul testing and standard solutions were respectively sucked with accuracy, injected into the HPLC and measured.

The results were shown below.

TABLE 1 investigation of extracting Radix Paeoniae alba alone or in combination

| Process | Paeoniflorin content (mg/g) | Yield rate (%) | Dissolvability |
|---|---|---|---|
| $1^{st}$ process | 15.58 | 20.63 | Totally dissolved, good dissolvability |
| $2^{nd}$ process | 15.10 | 21.88 | Black residues, somewhat less dissolvability |

As shown in the results, in terms of the paeoniflorin content, the extract prepared by extracting Radix Paeoniae alba alone was slightly higher than that in combination (3.18%). In terms of the yield rate, the former was less than the latter. In terms of the dissolvability, the former was much better than the latter. Compared with the latter one, the former process had advantages of shorter concentration heating time, less paeoniflorin loss, increased transfer rate, and elevated content in product. Thus, considering various factors comprehensively, the process by extracting Radix Paeoniae alba alone was reasonable.

3. Investigation of Extracting Ramulus Uncariae Cum Uncis in Different Ways

Rhynchophylline content and yield rate were used as indicators for investigation of extracting Ramulus Uncariae cum Uncis in different ways (where Ramulus Uncariae cum Uncis is decocted earlier or later). A mixture of Radix Rehmanniae Preparata, Caulis Spatholobi, Spica Prunellae, Concha Margaritifera Usta, Ramulus Uncariae cum Uncis and Herba Asari was taken at prescription dose. Production processes were designed respectively. $1^{st}$ process was that aforesaid mixture was added with 6 fold of water, extracted for 3 times to have the extract, the first time for 2 hours, the second and third times for 1 hour. $2^{nd}$ process was that Radix Rehmanniae Preparata, Caulis Spatholobi, Spica Prunellae and Concha Margaritifera Usta were added with 6 fold of water, extracted for 2 hours, filtered, and the resultant residues were mixed with the Ramulus Uncariae cum Uncis, extracted twice with 6 fold of water, each for 1 hour to have the extract. Rhynchophylline content and yield rate of aforeobtained extracts were measured respectively.

Method for Determination of Rhynchophylline
Apparatus and Reagent

Agilent 1100 HPLC was equipped with quaternary pump, DAD, automatic sampler, online degasser and column thermostat.

Standard rhynchophylline, methanol (chromatographically pure), purified water, triethylamine, glacial acetic acid (analytically pure)

Chromatographic conditions: Agilent Zorbax SB-$C_{18}$ column (250 mm×4.6 mm, 5 μm)

Mobile phase: methanol-10 mmol triethylamine solution (48:52), adjusted to pH=5.0 with acetic acid Flow rate: 1.0 ml/min; column temperature: 30° C.; detection wavelength: 254 nm Preparation of standard solution: appropriate quantity of standard rhynchophylline was taken and weighed accurately to prepare the standard solution (with 1 ml solution containing 10 μg solute) by adding methanol.

Preparation of testing solution: appropriate quantity (approximately equal to 2 g crude medicine Ramulus Uncariae cum Uncis) of combined water extract was sucked, alkalified by adding 5 ml ammonia water, extracted with chloroform for 3 times and combined, evaporated to dryness with water bath. The residues were dissolved by adding methanol to volume of 20 ml, filtered to give the testing solution.

Measuring method: 10 μl testing and standard solutions were respectively sucked with accuracy, injected into the HPLC and measured.

The results were shown below.

TABLE 2 investigation of extracting Ramulus Uncariae cum Uncis in different ways

| Process | rhynchophylline content (mg) | Yield rate (%) |
|---|---|---|
| $1^{st}$ process | 10.80 | 13.39 |
| $2^{nd}$ process | 10.92 | 12.96 |

As shown in the results, in terms of the rhynchophylline content, the extract prepared by $1^{st}$ process was almost the same as that by $2^{nd}$ process. In terms of the yield rate, the extract prepared by $1^{st}$ process was slightly higher than that by $2^{nd}$ process, but the difference was slight. The inconvenient operation brought by $2^{nd}$ process should be considered, for example the medicine perhaps floated on the surface, which may influence extraction and cause potential safety hazard. Due to its simplified process, easy operation and enhanced safety, the $1^{st}$ process was reasonable.

As shown in pharmacological research, it is confirmed that said pharmaceutical composition has effects of ameliorating cerebral pial microcirculation, increasing cerebral blood flow, relaxing vasospasm and stopping pain. As shown in pharmacodynamics experiment, compared with the one prepared by methods known in prior arts, the pharmaceutical composition has an excellent effect of treating headache.

EMBODIMENTS

Example 1

The following medicinal materials were taken: 253.5 g of Radix Angelicae Sinensis, 253.5 g of Rhizoma Chuanxiong, 202.7 g of Radix Paeoniae alba, 202.7 g of Radix Rehmanniae Preparata, 506.8 g of Ramulus Uncariae cum Uncis, 506.8 g of Caulis Spatholobi, 506.8 g of Spica Prunellae, 506.8 g of Semen Cassiae, 506.8 g of Concha Margaritifera Usta, 253.5 g of Rhizoma Corydalis and 50.5 g of Herba Asari.

Preparation of #1 Extract: Radix Angelicae Sinensis, Rhizoma Chuanxiong, Rhizoma Corydalis and Semen Cassiae were mixed, extracted by using heating refluxing for 2 times with 4 fold of 70% ethanol, the first time for 2 hours and the second time for 1 hour, and filtered to remove the impurities; and the ethanol was recovered and concentrated until the relative density was 1.300~1.310 (74~76° C.) to give 253 g of #1 Extract for later use.

Preparation of #2 Extract: *Radix Paeoniae alba* was added with 4 fold of 60% ethanol, soaked, extracted by using heating refluxing for 2 times, the first time for 2 hours and the second time for 1 hour, and filtered; and the ethanol was recovered and concentrated until the relative density is 1.23~1.33 (65° C.) to give 42 g of #2 Extract for later use.

Preparation of #3 Extract: *Radix Rehmanniae Preparata, Ramulus Uncariae cum Uncis, Caulis Spatholobi, Spica Prunellae, Concha Margaritifera Usta* and *Herba Asari* were mixed, decocted for 2 times with 5 fold of water, the first time for 2 hours and the second time for 1 hour, filtered, concentrated until the relative density was 1.06~1.10 (80° C.), into which ethanol was added to make a final ethanol content of 65~70%, left to stand still for 12~24 hours, and filtered; and the ethanol was recovered and concentrated until the relative density was 1.320~1.325 (79~81° C.) to give 305 g of #3 Extract for later use.

300 g of dextrin was dissolved with purified water, into which 3.0 g steviosin was added to dissolve by well stirring to give slurry. 600 g of well-prepared three Extracts were added into the slurry and stirred stepwise. The density of resultant slurry was adjusted to 1.12~1.23 (42~45° C.), and the slurry was online filtered with 60~100 mesh sifter.

250.0 g rest of the dextrin was put into the granulator. A series of parameters were adjusted, e.g. fan frequency, temperature of inlet air, frequency of liquid feed and spray pressure, to make materials in well-fluidized state in the fluid bed. The materials were spray-granulated at a temperature of 30~60° C., and dried. The temperature was further increased to 80~90° C. to thoroughly dry.

The resultant granules were sorted, sifted and totally mixed to produce granules. The package was aluminum-plastic composite film pillow bag with specification of 4 g/bag.

Example 2

The following medicinal materials were taken: 338 g of *Radix Angelicae Sinensis*, 338 g of *Rhizoma Chuanxiong*, 270.3 g of *Radix Paeoniae alba*, 270.3 g of *Radix Rehmanniae Preparata*, 675.7 g of *Ramulus Uncariae cum Uncis*, 675.7 g of *Caulis Spatholobi*, 675.7 g of *Spica Prunellae*, 675.7 g of *Semen Cassiae*, 675.7 g of *Concha Margaritifera Usta*, 338 g of *Rhizoma Corydalis* and 67.3 g of *Herba Asari*.

Preparation of #1 Extract: *Radix Angelicae Sinensis, Rhizoma Chuanxiong, Rhizoma Corydalis* and *Semen Cassiae* were mixed, extracted by using heating refluxing for 2 times with 4 fold of 70% ethanol, the first time for 2 hours and the second time for 1 hour, and filtered to remove the impurities; and the ethanol was recovered and concentrated until the relative density was 1.300~1.310 (74~76° C.) to give 335 g of #1 Extract for later use.

Preparation of #2 Extract: *Radix Paeoniae alba* was added with 4 fold of 60% ethanol, soaked, extracted by using heating refluxing for 2 times, the first time for 2 hours and the second time for 1 hour, and filtered; and the ethanol was recovered and concentrated until the relative density was 1.23~1.33 (65° C.) to give 55 g of #2 Extract for later use.

Preparation of #3 Extract: *Radix Rehmanniae Preparata, Ramulus Uncariae cum Uncis, Caulis Spatholobi, Spica Prunellae, Concha Margaritifera Usta* and *Herba Asari* were mixed, decocted for 2 times with 5 fold of water, the first time for 2 hours and the second time for 1 hour, filtered, concentrated until the relative density was 1.06~1.10 (80° C.), into which ethanol was added to make a final ethanol content of 65~72%, left to stand still for 12~24 hours, and filtered; and the ethanol was recovered and concentrated until the relative density was 1.320~1.325 (79~81° C.) to give 420 g of #3 Extract for later use.

83 g of sucrose was dissolved with purified water by well stirring to give the slurry. 810 g of well-prepared three Extracts were added into the slurry and stirred stepwise. The density of resultant slurry was adjusted to 1.12~1.23 (42~45° C.), and the slurry was online filtered with 60~100 mesh sifter.

320 g rest of the sucrose was put into the granulator. A series of parameters were adjusted, e.g. fan frequency, temperature of inlet air, frequency of liquid feed and spray pressure, to make materials in well-fluidized state in the fluid bed. The materials were spray-granulated at a temperature of 30~60° C., and dried. The temperature was further increased to 70~90° C. to thoroughly dry.

The resultant granules were sorted, sifted and totally mixed to produce granules. The package was aluminum-plastic composite film pillow bag with specification of 3 g/bag.

Example 3

The following medicinal materials were taken: 150 g of *Radix Angelicae Sinensis*, 150 g of *Rhizoma Chuanxiong*, 225 g of *Radix Paeoniae alba*, 225 g of *Radix Rehmanniae Preparata*, 551 g of *Ramulus Uncariae cum Uncis*, 551 g of *Caulis Spatholobi*, 551 g of *Spica Prunellae*, 551 g of *Semen Cassiae*, 551 g of *Concha Margaritifera Usta*, 225 g of *Rhizoma Corydalis* and 19 g of *Herba Asari*.

Preparation of #1 Extract: *Radix Angelicae Sinensis, Rhizoma Chuanxiong, Rhizoma Corydalis* and *Semen Cassiae* were mixed, extracted by using heating refluxing for 2 times with 5 fold of 70% ethanol, the first time for 2.5 hours and the second time for 1 hour, and filtered to remove the impurities; and the ethanol was recovered and concentrated until the relative density was 1.250~1.310 (70~74° C.) to give 210 g of #1 Extract for later use.

Preparation of #2 Extract: *Radix Paeoniae alba* was added with 4 fold of 80% ethanol, soaked, extracted by using heating refluxing for 2 times, the first time for 2 hours and the second time for 1 hour, and filtered; and the ethanol was recovered and concentrated until the relative density was 1.15~1.25 (65° C.) to give 50 g of #2 Extract for later use.

Preparation of #3 Extract: *Radix Rehmanniae Preparata, Ramulus Uncariae cum Uncis, Caulis Spatholobi, Spica Prunellae, Concha Margaritifera Usta* and *Herba Asari* were mixed, decocted for 2 times with 5 fold of water, the first time for 2 hours and the second time for 1 hour, filtered, concentrated until the relative density was 1.06~1.10 (80° C.), into which ethanol was added to make a final ethanol content of 60~65%, left to stand still for 12~24 hours, and filtered; and the ethanol was recovered and concentrated until the relative density was 1.27~1.320 (75~80° C.) to give 545 g of #3 Extract for later use.

231 g of dextrin was dissolved with purified water, into which 3.0 g steviosin was added to dissolve by well stirring to give the slurry. 805 g of well-prepared three Extracts were added into the slurry and stirred stepwise. The density of resultant slurry was adjusted to 1.12~1.23 (42~50° C.), and the slurry was online filtered with 60~100 mesh sifter.

151 g rest of the dextrin was put into the granulator. A series of parameters were adjusted, e.g. fan frequency, temperature of inlet air, frequency of liquid feed and spray pressure, to make materials in well-fluidized state in the fluid bed. The materials were spray-granulated at a temperature of 30~60° C., and dried. The temperature was further increased to 70~90° C. to thoroughly dry.

The resultant granules were sorted, sifted and totally mixed to produce granules. The package was aluminum-plastic composite film pillow bag with specification of 4 g/bag.

Example 4

The following medicinal materials were taken: 250 g of *Radix Angelicae Sinensis*, 250 g of *Rhizoma Chuanxiong*, 250 g of *Radix Paeoniae alba*, 250 g of *Radix Rehmanniae Preparata*, 740 g of *Ramulus Uncariae cum Uncis*, 740 g of *Caulis Spatholobi*, 740 g of *Spica Prunellae*, 740 g of *Semen Cassiae*, 740 g of *Concha Margaritifera Usta*, 250 g of *Rhizoma Corydalis* and 50 g of *Herba Asari*.

Preparation of #1 Extract: *Radix Angelicae Sinensis*, *Rhizoma Chuanxiong*, *Rhizoma Corydalis* and *Semen Cassiae* were mixed, extracted by using heating refluxing for 2 times with 4 fold of 80% ethanol, the first time for 2.5 hours and the second time for 1 hour, and filtered to remove the impurities; and the ethanol was recovered and concentrated until the relative density was 1.300~1.350 (75~80° C.) to give 300 g of #1 Extract for later use.

Preparation of #2 Extract: *Radix Paeoniae alba* was added with 6 fold of 60% ethanol, soaked, extracted by using heating refluxing for 3 times, the first time for 3 hours and the second time for 1 hour and the third time for 0.5 hour, and filtered; and the ethanol was recovered and concentrated until the relative density was 1.20~1.35 (60° C.) to give 60 g of #2 Extract for later use.

Preparation of #3 Extract: *Radix Rehmanniae Preparata*, *Ramulus Uncariae cum Uncis*, *Caulis Spatholobi*, *Spica Prunellae*, *Concha Margaritifera Usta* and *Herba Asari* were mixed, decocted for 2 times with 8 fold of water, the first time for 3 hours and the second time for 2 hours, filtered, concentrated until the relative density was 1.06~1.10 (80° C.), into which ethanol was added to make a final ethanol content of 80~85%, left to stand still for 12~24 hours, and filtered; and the ethanol was recovered and concentrated until the relative density was 1.30~1.350 (80~85° C.) to give 425 g of #3 Extract for later use.

80 g of soluble starch was dissolved with purified water, into which 3 g steviosin was added to dissolve by well stirring to give the slurry. 785 g of well-prepared three Extracts were added into the slurry and stirred stepwise. The density of resultant slurry was adjusted to 1.12~1.23 (42~50° C.), and the slurry was online filtered with 60~100 mesh sifter.

330 g rest of the soluble starch was put into the granulator. A series of parameters were adjusted, e.g. fan frequency, temperature of inlet air, frequency of liquid feed and spray pressure, to make materials in well-fluidized state in the fluid bed. The materials were spray-granulated at a temperature of 30~60° C., and dried. The temperature was further increased to 70~90° C. to thoroughly dry.

The resultant granules were sorted, sifted and totally mixed to produce granules. The package was aluminum-plastic composite film pillow bag with specification of 3 g/bag.

Example 5

The following medicinal materials were taken: 338 g of *Radix Angelicae Sinensis*, 338 g of *Rhizoma Chuanxiong*, 75 g of *Radix Paeoniae alba*, 75 g of *Radix Rehmanniae Preparata*, 510 g of *Ramulus Uncariae cum Uncis*, 510 g of *Caulis Spatholobi*, 510 g of *Spica Prunellae*, 510 g of *Semen Cassiae*, 510 g of *Concha Margaritifera Usta*, 337 g of *Rhizoma Corydalis* and 37 g of *Herba Asari*.

Preparation of #1 Extract: *Radix Angelicae Sinensis*, *Rhizoma Chuanxiong*, *Rhizoma Corydalis* and *Semen Cassiae* were mixed, extracted by using heating refluxing for 2 times with 4 fold of 50% ethanol, the first time for 2 hours and the second time for 2 hours, and filtered to remove the impurities; and the ethanol was recovered and concentrated until the relative density was 1.300~1.350 (73~78° C.) to give 330 g of #1 Extract for later use.

Preparation of #2 Extract: *Radix Paeoniae alba* was added with 5 fold of 70% ethanol, soaked, extracted by using heating refluxing for 2 times, the first time for 1 hour and the second time for 1 hour, and filtered; and the ethanol was recovered and concentrated until the relative density was 1.23~1.35 (65° C.) to give 15 g of #2 Extract for later use.

Preparation of #3 Extract: *Radix Rehmanniae Preparata*, *Ramulus Uncariae cum Uncis*, *Caulis Spatholobi*, *Spica Prunellae*, *Concha Margaritifera Usta* and *Herba Asari* were mixed, decocted for 2 times with 10 fold of water, the first time for 2 hours and the second time for 2 hours, filtered, concentrated until the relative density was 1.06~1.10 (80° C.), into which ethanol was added to make a final ethanol content of 63~70%, left to stand still for 12~24 hours, and filtered; and the ethanol was recovered and concentrated until the relative density was 1.290~1.330 (78~83° C.) to give 253 g of #3 Extract for later use.

320 g of dextrin was dissolved with purified water, into which 3 g steviosin was added to dissolve by well stirring to give the slurry. 598 g of well-prepared three Extracts were added into the slurry and stirred stepwise. The density of resultant slurry was adjusted to 1.12~1.23 (42~50° C.), and the slurry was online filtered with 60~100 mesh sifter.

240 g rest of the dextrin was put into the granulator. A series of parameters were adjusted, e.g. fan frequency, temperature of inlet air, frequency of liquid feed and spray pressure, to make materials in well-fluidized state in the fluid bed. The materials were spray-granulated at a temperature of 30~60° C., and dried. The temperature was further increased to 70~90° C. to thoroughly dry.

The resultant granules were sorted, sifted and totally mixed to produce granules. The package was aluminum-plastic composite film pillow bag with specification of 4 g/bag.

Example 6

The following medicinal materials were taken: 300 g of *Radix Angelicae Sinensis*, 300 g of *Rhizoma Chuanxiong*, 400 g of *Radix Paeoniae alba*, 400 g of *Radix Rehmanniae Preparata*, 650 g of *Ramulus Uncariae cum Uncis*, 650 g of *Caulis Spatholobi*, 650 g of *Spica Prunellae*, 650 g of *Semen Cassiae*, 650 g of *Concha Margaritifera Usta*, 300 g of *Rhizoma Corydalis* and 50 g of *Herba Asari*.

Preparation of #1 Extract: *Radix Angelicae Sinensis*, *Rhizoma Chuanxiong*, *Rhizoma Corydalis* and *Semen Cassiae* were mixed, extracted by using heating refluxing for 3 times with 3 fold of 60% ethanol, the first time for 2 hours, the second time for 1 hour and the third time for 0.5 hour, and filtered to remove the impurities; and the ethanol was recovered and concentrated until the relative density was 1.29~1.340 (73~78° C.) to give 315 g of #1 Extract for later use.

Preparation of #2 Extract: *Radix Paeoniae alba* was added with 4 fold of 80% ethanol, soaked, extracted by using heating refluxing for 3 times, the first time for 2 hours, the second time for 1 hour and the third time for 1 hour, and filtered; and the ethanol was recovered and concentrated until the relative density was 1.18~1.33 (65° C.) to give 90 g of #2 Extract for later use.

Preparation of #3 Extract: *Radix Rehmanniae Preparata, Ramulus Uncariae cum Uncis, Caulis Spatholobi, Spica Prunellae, Concha Margaritifera Usta* and *Herba Asari* were mixed, decocted for 2 times with 7 fold of water, the first time for 2 hours and the second time for 1 hour, filtered, concentrated until the relative density was 1.06~1.10 (80° C.), into which ethanol was added to make a final ethanol content of 70~75%, left to stand still for 12~24 hours, and filtered; and the ethanol was recovered and concentrated until the relative density was 1.310~1.330 (77~82° C.) to give 375 g of #3 Extract for later use.

84 g of dextrin was dissolved with purified water, into which 3 g steviosin was added to dissolve by well stirring to give the slurry. 780 g of well-prepared three Extracts were added into the slurry and stirred stepwise. The density of resultant slurry was adjusted to 1.12~1.23 (42~50° C.), and the slurry was online filtered with 60~100 mesh sifter.

336 g rest of the dextrin was put into the granulator. A series of parameters were adjusted, e.g. fan frequency, temperature of inlet air, frequency of liquid feed and spray pressure, to make materials in well-fluidized state in the fluid bed. The materials were spray-granulated at a temperature of 30~60° C., and dried. The temperature was further increased to 70~90° C. to thoroughly dry.

The resultant granules were sorted, sifted and totally mixed to produce granules. The package was aluminum-plastic composite film pillow bag with specification of 3 g/bag.

Example 7

The following medicinal materials were taken: 338 g of *Radix Angelicae Sinensis*, 338 g of *Rhizoma Chuanxiong*, 300 g of *Radix Paeoniae alba*, 300 g of *Radix Rehmanniae Preparata*, 413 g of *Ramulus Uncariae cum Uncis*, 413 g of *Caulis Spatholobi*, 413 g of *Spica Prunellae*, 413 g of *Semen Cassiae*, 413 g of *Concha Margaritifera Usta*, 337 g of *Rhizoma Corydalis* and 75 g of *Herba Asari*.

Preparation of #1 Extract: *Radix Angelicae Sinensis, Rhizoma Chuanxiong, Rhizoma Corydalis* and *Semen Cassiae* were mixed, extracted by using heating refluxing for 2 times with 6 fold of 70% ethanol, the first time for 2 hours and the second time for 0.5 hour, and filtered to remove the impurities; and the ethanol was recovered and concentrated until the relative density was 1.260~1.310 (74~76° C.) to give 300 g of #1 Extract for later use.

Preparation of #2 Extract: *Radix Paeoniae alba* was added with 6 fold of 60% ethanol, soaked, extracted by using heating refluxing for 2 times, the first time for 2 hours and the second time for 2 hours, and filtered; and the ethanol was recovered and concentrated until the relative density was 1.21~1.34 (55° C.) to give 70 g of #2 Extract for later use.

Preparation of #3 Extract: *Radix Rehmanniae Preparata, Ramulus Uncariae cum Uncis, Caulis Spatholobi, Spica Prunellae, Concha Margaritifera Usta* and *Herba Asari* were mixed, decocted for 2 times with 6 fold of water, the first time for 2 hours and the second time for 1 hour, filtered, concentrated until the relative density was 1.06~1.10 (80° C.), into which ethanol was added to make a final ethanol content of 65~75%, left to stand still for 12~24 hours, and filtered; and the ethanol was recovered and concentrated until the relative density was 1.300~1.300 (79~81° C.) to give 424 g of #3 Extract for later use.

40 g of dextrin was dissolved with purified water, into which 3 g steviosin was added to dissolve by well stirring to give the slurry. 794 g of well-prepared three Extracts were added into the slurry and stirred stepwise. The density of resultant slurry was adjusted to 1.12~1.23 (42~50° C.), and the slurry was online filtered with 60~100 mesh sifter.

163 g rest of the dextrin was put into the granulator. A series of parameters were adjusted, e.g. fan frequency, temperature of inlet air, frequency of liquid feed and spray pressure, to make materials in well-fluidized state in the fluid bed. The materials were spray-granulated at a temperature of 30~60° C., and dried. The temperature was further increased to 70~90° C. to thoroughly dry.

The resultant granules were sorted, sifted and totally mixed to produce granules. The package was aluminum-plastic composite film pillow bag with specification of 4 g/bag.

Example 8

The following medicinal materials were taken: 450 g of *Radix Angelicae Sinensis*, 450 g of *Rhizoma Chuanxiong*, 350 g of *Radix Paeoniae alba*, 350 g of *Radix Rehmanniae Preparata*, 570 g of *Ramulus Uncariae cum Uncis*, 570 g of *Caulis Spatholobi*, 570 g of *Spica Prunellae*, 570 g of *Semen Cassiae*, 570 g of *Concha Margaritifera Usta*, 450 g of *Rhizoma Corydalis* and 100 g of *Herba Asari*.

Preparation of #1 Extract: *Radix Angelicae Sinensis, Rhizoma Chuanxiong, Rhizoma Corydalis* and *Semen Cassiae* were mixed, extracted by using heating refluxing for 2 times with 6 fold of 80% ethanol, the first time for 1 hour and the second time for 1 hour, and filtered to remove the impurities; and the ethanol was recovered and concentrated until the relative density was 1.29~1.340 (73~78° C.) to give 390 g of #1 Extract for later use.

Preparation of #2 Extract: *Radix Paeoniae alba* was added with 3 fold of 60% ethanol, soaked, extracted by using heating refluxing for 2 times, the first time for 2.5 hours and the second time for 2 hours, and filtered; and the ethanol was recovered and concentrated until the relative density was 1.17~1.33 (65° C.) to give 65 g of #2 Extract for later use.

Preparation of #3 Extract: *Radix Rehmanniae Preparata, Ramulus Uncariae cum Uncis, Caulis Spatholobi, Spica Prunellae, Concha Margaritifera Usta* and *Herba Asari* were mixed, decocted for 2 times with 9 fold of water, the first time for 3 hours and the second time for 3 hours, filtered, concentrated until the relative density was 1.06~1.08 (80° C.), into which ethanol was added to make a final ethanol content of 65~75%, left to stand still for 12~22 hours, and filtered; and the ethanol was recovered and concentrated until the relative density was 1.310~1.330 (77~82° C.) to give 385 g of #3 Extract for later use.

110 g of dextrin was dissolved with purified water, into which 3 g steviosin was added to dissolve by well stirring to give the slurry. 840 g of well-prepared three Extracts were added into the slurry and stirred stepwise. The density of resultant slurry was adjusted to 1.12~1.23 (42~50° C.), and the slurry was online filtered with 60~100 mesh sifter.

256 g rest of the dextrin was put into the granulator. A series of parameters were adjusted, e.g. fan frequency, temperature of inlet air, frequency of liquid feed and spray pressure, to make materials in well-fluidized state in the fluid bed. The materials were spray-granulated at a temperature of 30~60° C., and dried. The temperature was further increased to 70~90° C. to thoroughly dry.

The resultant granules were sorted, sifted and totally mixed to produce granules. The package was aluminum-plastic composite film pillow bag with specification of 3 g/bag.

Example 9

The following medicinal materials were taken: 253.5 g of *Radix Angelicae Sinensis*, 253.5 g of *Rhizoma Chuanxiong*, 202.7 g of *Radix Paeoniae alba*, 202.7 g of *Radix Rehmanniae Preparata*, 506.8 g of *Ramulus Uncariae cum Uncis*, 506.8 g of *Caulis Spatholobi*, 506.8 g of *Spica Prunellae*, 506.8 g of *Semen Cassiae*, 506.8 g of *Concha Margaritifera Usta*, 253.5 g of *Rhizoma Corydalis* and 50.5 g of *Herba Asari*.

Preparation of #1 Extract: *Radix Angelicae Sinensis*, *Rhizoma Chuanxiong*, *Rhizoma Corydalis* and *Semen Cassiae* were mixed, extracted by using heating refluxing for 2 times with 4 fold of 70% ethanol, the first time for 2 hours and the second time for 1 hour, and filtered to remove the impurities; and the ethanol was recovered and concentrated until the relative density was 1.250~1.310 (70~74° C.) to give 253 g of #1 Extract for later use.

Preparation of #2 Extract: *Radix Paeoniae alba* was added with 4 fold of 60% ethanol, soaked, extracted by using heating refluxing for 2 times, the first time for 2 hours and the second time for 1 hour, and filtered; and the ethanol was recovered and concentrated until the relative density was 1.23~1.33 (65° C.) to give 42 g of #2 Extract for later use.

Preparation of #3 Extract: *Radix Rehmanniae Preparata*, *Ramulus Uncariae cum Uncis*, *Caulis Spatholobi*, *Spica Prunellae*, *Concha Margaritifera Usta* and *Herba Asari* were mixed, decocted for 2 times with 5 fold of water, the first time for 2 hours and the second time for 1 hour, filtered, concentrated until the relative density was 1.06~1.10 (80° C.), into which ethanol was added to make a final ethanol content of 65~75%, left to stand still for 12~24 hours, and filtered; and the ethanol was recovered and concentrated until the relative density was 1.27~1.320 (75~80° C.) to give 305 g of #3 Extract for later use.

300 g of soluble starch was dissolved with purified water, into which 3.0 g steviosin was added to dissolve by well stirring to give the slurry. 600 g of well-prepared three Extracts were added into the slurry and stirred stepwise. The density of resultant slurry was adjusted to 1.12~1.23 (42~50° C.), and the slurry was online filtered with 60~100 mesh sifter.

250.0 g rest of the soluble starch was put into the granulator. A series of parameters were adjusted, e.g. fan frequency, temperature of inlet air, frequency of liquid feed and spray pressure, to make materials in well-fluidized state in the fluid bed. The materials were spray-granulated at a temperature of 30~60° C., and dried. The temperature was further increased to 80~90° C. to thoroughly dry.

The resultant granules were sorted, sifted and totally mixed to produce granules. The package was aluminum-plastic composite film pillow bag with specification of 4 g/bag.

Example 10

The following medicinal materials were taken: 338 g of *Radix Angelicae Sinensis*, 338 g of *Rhizoma Chuanxiong*, 270.3 g of *Radix Paeoniae alba*, 270.3 g of *Radix Rehmanniae Preparata*, 675.7 g of *Ramulus Uncariae cum Uncis*, 675.7 g of *Caulis Spatholobi*, 675.7 g of *Spica Prunellae*, 675.7 g of *Semen Cassiae*, 675.7 g of *Concha Margaritifera Usta*, 338 g of *Rhizoma Corydalis* and 67.3 g of *Herba Asari*.

Preparation of #1 Extract: *Radix Angelicae Sinensis*, *Rhizoma Chuanxiong*, *Rhizoma Corydalis* and *Semen Cassiae* were mixed, extracted by using heating refluxing for 2 times with 4 fold of 70% ethanol, the first time for 2 hours and the second time for 1 hour, and filtered to remove the impurities; and the ethanol was recovered and concentrated until the relative density was 1.280~1.320 (75~80° C.) to give 335 g of #1 Extract for later use.

Preparation of #2 Extract: *Radix Paeoniae alba* was added with 4 fold of 60% ethanol, soaked, extracted by using heating refluxing for 2 times, the first time for 2 hours and the second time for 1 hour, and filtered; and the ethanol was recovered and concentrated until the relative density was 1.23~1.33 (65° C.) to give 55 g of #2 Extract for later use.

Preparation of #3 Extract: *Radix Rehmanniae Preparata*, *Ramulus Uncariae cum Uncis*, *Caulis Spatholobi*, *Spica Prunellae*, *Concha Margaritifera Usta* and *Herba Asari* were mixed, decocted for 2 times with 5 fold of water, the first time for 2 hours and the second time for 1 hour, filtered, concentrated until the relative density was 1.06~1.10 (80° C.), into which ethanol was added to make a final ethanol content of 60~65%, left to stand still for 12~24 hours, and filtered; and the ethanol was recovered and concentrated until the relative density was 1.315~1.320 (76~79° C.) to give 420 g of #3 Extract for later use.

80 g of microcrystalline cellulose was dissolved with purified water, into which 3.0 g aspartame was added to dissolve by well stirring to give the slurry. 810 g of well-prepared three Extracts were added into the slurry and stirred stepwise. The density of resultant slurry was adjusted to 1.12~1.23 (42~50° C.), and the slurry was online filtered with 60~100 mesh sifter.

320 g rest of the microcrystalline cellulose was put into the granulator. A series of parameters were adjusted, e.g. fan frequency, temperature of inlet air, frequency of liquid feed and spray pressure, to make materials in well-fluidized state in the fluid bed. The materials were spray-granulated at a temperature of 30~60° C., and dried. The temperature was further increased to 70~90° C. to thoroughly dry.

The resultant granules were sorted, sifted and totally mixed to produce granules. The package was aluminum-plastic composite film pillow bag with specification of 3 g/bag.

Example 11

The following medicinal materials were taken: 150 g of *Radix Angelicae Sinensis*, 150 g of *Rhizoma Chuanxiong*, 225 g of *Radix Paeoniae alba*, 225 g of *Radix Rehmanniae Preparata*, 551 g of *Ramulus Uncariae cum Uncis*, 551 g of *Caulis Spatholobi*, 551 g of *Spica Prunellae*, 551 g of *Semen Cassiae*, 551 g of *Concha Margaritifera Usta*, 225 g of *Rhizoma Corydalis* and 19 g of *Herba Asari*.

Preparation of #1 Extract: *Radix Angelicae Sinensis*, *Rhizoma Chuanxiong*, *Rhizoma Corydalis* and *Semen Cassiae* were mixed, extracted by using heating refluxing for 2 times with 5 fold of 70% ethanol, the first time for 2.5 hours and the second time for 1 hour, and filtered to remove the impurities; and the ethanol was recovered and concentrated until the relative density was 1.290~1.300 (75~77° C.) to give 210 g of #1 Extract for later use.

Preparation of #2 Extract: *Radix Paeoniae alba* was added with 4 fold of 80% ethanol, soaked, extracted by using heating refluxing for 2 times, the first time for 2 hours and the second time for 2 hours, and filtered; and the ethanol was recovered and concentrated until the relative density was 1.15~1.25 (65° C.) to give 50 g of #2 Extract for later use.

Preparation of #3 Extract: *Radix Rehmanniae Preparata, Ramulus Uncariae cum Uncis, Caulis Spatholobi, Spica Prunellae, Concha Margaritifera Usta* and *Herba Asari* were mixed, decocted for 2 times with 5 fold of water, the first time for 2 hours and the second time for 1 hour, filtered, concentrated until the relative density was 1.06~1.10 (80° C.), into which ethanol was added to make a final ethanol content of 65~70%, left to stand still for 12~24 hours, and filtered; and the ethanol was recovered and concentrated until the relative density was 1.310~1.315 (79~82° C.) to give 545 g of #3 Extract for later use.

231 g of lactose was dissolved with purified water, into which 3.0 g aspartame was added to dissolve by well stirring to give the slurry. 805 g of well-prepared three Extracts were added into the slurry and stirred stepwise. The density of resultant slurry was adjusted to 1.12~1.23 (42~50° C.), and the slurry was online filtered with 60~100 mesh sifter.

151 g rest of the lactose was put into the granulator. A series of parameters were adjusted, e.g. fan frequency, temperature of inlet air, frequency of liquid feed and spray pressure, to make materials in well-fluidized state in the fluid bed. The materials were spray-granulated at a temperature of 30~60° C., and dried. The temperature was further increased to 70~90° C. to thoroughly dry.

The resultant granules were sorted, sifted and totally mixed to produce granules. The package was aluminum-plastic composite film pillow bag with specification of 4 g/bag.

Example 12

The following medicinal materials were taken: 250 g of *Radix Angelicae Sinensis*, 250 g of *Rhizoma Chuanxiong*, 250 g of *Radix Paeoniae alba*, 250 g of *Radix Rehmanniae Preparata*, 740 g of *Ramulus Uncariae cum Uncis*, 740 g of *Caulis Spatholobi*, 740 g of *Spica Prunellae*, 740 g of *Semen Cassiae*, 740 g of *Concha Margaritifera Usta*, 250 g of *Rhizoma Corydalis* and 50 g of *Herba Asari*.

Preparation of #1 Extract: *Radix Angelicae Sinensis, Rhizoma Chuanxiong, Rhizoma Corydalis* and *Semen Cassiae* were mixed, extracted by using heating refluxing for 2 times with 4 fold of 80% ethanol, the first time for 2.5 hours and the second time for 1 hour, and filtered to remove the impurities; and the ethanol was recovered and concentrated until the relative density was 1.280~1.300 (75~77° C.) to give 300 g of #1 Extract for later use.

Preparation of #2 Extract: *Radix Paeoniae alba* was added with 6 fold of 60% ethanol, soaked, extracted by using heating refluxing for 3 times, the first time for 2 hours, the second time for 1 hour and the third time for 0.5 hour, and filtered; and the ethanol was recovered and concentrated until the relative density was 1.20~1.35 (60° C.) to give 60 g of #2 Extract for later use.

Preparation of #3 Extract: *Radix Rehmanniae Preparata, Ramulus Uncariae cum Uncis, Caulis Spatholobi, Spica Prunellae, Concha Margaritifera Usta* and *Herba Asari* were mixed, decocted for 2 times with 8 fold of water, the first time for 3 hours and the second time for 2 hour, filtered, concentrated until the relative density was 1.06~1.10 (80° C.), into which ethanol was added to make a final ethanol content of 80~85%, left to stand still for 12~24 hours, and filtered; and the ethanol was recovered and concentrated until the relative density was 1.280~1.330 (75~80° C.) to give 425 g of #3 Extract for later use.

80 g of dextrin was dissolved with purified water, into which 3 g aspartame was added to dissolve by well stirring to give the slurry. 785 g of well-prepared three Extracts were added into the slurry and stirred stepwise. The density of resultant slurry was adjusted to 1.12~1.23 (42~50° C.), and the slurry was online filtered with 60~100 mesh sifter.

330 g rest of the dextrin was put into the granulator. A series of parameters were adjusted, e.g. fan frequency, temperature of inlet air, frequency of liquid feed and spray pressure, to make materials in well-fluidized state in the fluid bed. The materials were spray-granulated at a temperature of 30~60° C., and dried. The temperature was further increased to 70~90° C. to thoroughly dry.

The resultant granules were sorted, sifted and totally mixed to produce granules. The package was aluminum-plastic composite film pillow bag with specification of 3 g/bag.

Beneficial effects of said pharmaceutical compositions on treating headache have been demonstrated by following 2 pharmacodynamic researches.

Pharmacodynamic Research 1. Ameliorating Effect of Pharmaceutical Composition (YXQN) on Nitroglycerin-Induced Migraine in Rats 1. Materials 1.1 Animals: SD rats, male, weighing 180-200 g were provided by Beijing Weitonglihua Experimental Animal Technology Co., Ltd. The animals were raised in separate cages under natural light with excellent ventilation and free access to water and food. Animal diet was pellet feed purchased from Jinan Dakang Feed Inc. (Certificate No.: 364). Feeding environment for test animals was in accordance with the *Regulation of Test Animals Tianjin*.

1.2 Drug: tested drug was prepared by the method of Example 1 (YXQN-1), and comparison drug by the method of Chinese patent ZL200510073290.3 (YXQN-2). Both were provided by Tasly Pharmaceutical Co., Ltd. Qiyeanshen tablet (Approval. No.: Z45022054), as a positive control drug, was produced by Guangxi Beihai Pharmaceutical Co., Ltd (LOT: 20130123). Daily dosage: 20 mg per day.

1.3 Reagent: NOS assay kit, Coomassie brilliant blue protein assay kit and NO assay kit were purchased from Nanjing Jiancheng Science & technology Co., Ltd (LOT: 20120726), Rat 5-HT kit was purchased from Shanghai Jianglai Bio-tech Co., Ltd (LOT: 12-05), ELISA kit was purchased from Shanghai Meilian Bio-tech Co., Ltd and rat DA ELISA kit was purchased from Shanghai Kaibo Bio-tech Co., Ltd. Normal saline and 10% chloral hydrate.

1.4 Apparatus: Shimadzu UV2100 ultraviolet spectrophotometer, FLUKO F6/10 high-shearing dispersion emulsifier, Hettich ROTANTA 460R high-speed refrigerated centrifuge, Electronic balance and ultrasound Doppler blood stream detector.

2. Method 2.1 Grouping and Administration

Animals were randomly divided into 9 groups according to body weight, 10 rats in each group: the model group; positive control group; blank control group; high, middle and low dosage groups of YXQN-1 (1.562 g, 0.781 g and 0.391 extract/kg respectively); high, middle and low dosage groups of YXQN-2 (1.562 g, 0.781 g and 0.391 extract/kg respectively). Preventively, YXQN-1, YXQN-2 and positive control groups were administrated for 10 consecutive days.

Positive drug was given at a dosage of 20 mg per day. Equal volume of normal saline was intragastrically administrated to model group and blank control group.

2.2 Establishment of Behavior Observation Model

Except the blank control group, remaining rats received subcutaneous injection of nitroglycerin (10 ml/kg). Experimental migrainous rat models were duplicated. After administrated intragastrically, those rats, having two reddish ears and increased frequency of scratching head with forepaws, were taken as successful modeling. (1) Reddish ear: to observe the time the reddish ear appeared and disappeared after modeling; (2) Scratching head: to observe the frequency of scratching head every 30 min after modeling, the time scratching head appeared with consecutive scratching head for 5 times or more as the symbol, and the time scratching head disappeared with scratching head of less than 5 times during an interval, depression and fatigue as the symbol.

2.3 Determination of Bio-Marker

All animal models were made and administrated in light of aforesaid method. Blood and brain were collected 4 hours after modeling to prepare blood and brain homogenates, and frozen reserved for later use. Method of chemical colorimetry was performed in accordance with the label of the kit to assay NO content and NOS activity in serum; as well as 5-HT, 5-HIAA, NA DA contents in brain.

2.4 Statistical Management

All data were analyzed with SPSS 20.0 software, results were expressed as $\bar{x} \pm s$ and t-test was used between groups.

3. Results 3.1 Reddish Ears

No reddish ear was observed in blank control group. Reddish ears appeared in YXQN-1, YXQN-2 and model group 3 min after modeling. Compared with the model group, there was no significant difference in the time reddish ears appeared. After treatment, compared with the model group, the time reddish ears disappeared in middle and low dosage groups of YXQN-1 had statistical significance (P<0.05, P<0.01), however, no significant difference was found in the YXQN-2 groups. Compared with the equal dosage group of YXQN-2, the high and middle dosage groups of YXQN-1 had significant difference (P<0.05). The results were shown in Table 3.

TABLE 3 effect of YXQN-1 and YXQN-2 on the time reddish ears appeared and disappeared in rats (min, $\bar{x} \pm s$)

| Groups | n | Reddish ear appeared (min) | Reddish ear disappeared (min) |
|---|---|---|---|
| Blank control group | 10 | 0 | 0 |
| Model group | 10 | 3.28 ± 0.21 | 187.26 ± 10.44 |
| Qiyeanshen Tablet | 10 | 3.66 ± 0.50 | 109.45 ± 14.22* |
| YXQN-1 (High) | 10 | 3.55 ± 0.72 | 99.26 ± 15.28# |
| YXQN-1 (Middle) | 10 | 3.44 ± 0.52 | 111.87 ± 9.92**# |
| YXQN-1 (Low) | 10 | 3.15 ± 0.33 | 126.95 ± 9.10* |
| YXQN-2 (High) | 10 | 3.29 ± 0.60 | 125.49 ± 13.19 |
| YXQN-2 (middle) | 10 | 3.83 ± 0.86 | 135.99 ± 10.11 |
| YXQN-2 (Low) | 10 | 3.55 ± 0.19 | 138.95 ± 12.22 |

Compared with the model group, *P < 0.05, **P < 0.01; compared with YXQN-2, #P < 0.05.

3.2 Frequency of Scratching Head

In the blank control group, scratching head occasionally appeared once or twice during a few period of time. At about $3^{rd}$ min after modeling, scratching head appeared in YXQN-1, YXQN-2 and model groups, having no statistical significance, as compared with the model group. After treatment, there were more times of scratching head during period of $0^{th}$~$30^{th}$ min and $30^{th}$~$60^{th}$ min. Compared with the model group, the high, middle and low dosage groups of YXQN-1 had statistical significance (P<0.05, P<0.01) in frequency of scratching head. The significant difference had not yet been found in each dosage group of the YXQN-2. Compared with the equal dosage group of YXQN-2, the middle and low dosage groups of YXQN-1 had significant difference (P<0.05). The results were shown in Table 4.

TABLE 4 effect of YXQN-1 and YXQN-2 on the frequency of scratching head in rats ($\bar{x} \pm s$) during each period of time

| Group | N | Frequency (0~30 min) | Frequency (30~60 min) |
|---|---|---|---|
| Blank control group | 10 | 0 | 0 |
| Model group | 10 | 17.9 ± 1.1 | 86.4 ± 17.1 |
| Qiyeanshen Tablet | 10 | 6.1 ± 2.0** | 30.4 ± 2.7* |
| YXQN-1 (High) | 10 | 10.4 ± 2.9** | 26.9 ± 5.1** |
| YXQN-1 (Middle) | 10 | 12.1 ± 1.5*# | 37.3 ± 3.7*# |
| YXQN-1 (Low) | 10 | 13.3 ± 1.6*# | 49.6 ± 3.6*# |
| YXQN-2 (High) | 10 | 12.5 ± 2.4 | 45.9 ± 4.1 |
| YXQN-2 (middle) | 10 | 15.3 ± 2.5 | 50.2 ± 5.6 |
| YXQN-2 (Low) | 10 | 16.3 ± 2.8 | 55.5 ± 2.9 |

Compared with the model group, *P < 0.05, **P < 0.01; compared with YXQN-2, #P < 0.05.

3.3 Level of NO and NOS in Serum

Compared with the model group, the serum level of NO and NOS in rats in the high, middle and low dosage groups of YXQN-1 had statistical significance (P<0.05, P<0.01). The significant difference had not yet been found in each dosage group of the YXQN-2. Compared with the equal dosage group of YXQN-2, the middle and low dosage groups of YXQN-1 had significant difference (P<0.05). The results were shown in Table 5.

TABLET 5 effect of YXQN-1 and YXQN-2 on the serum level of NO and NOS in rats ($\bar{x} \pm s$)

| Group | N | NO (μmol/L) | NOS (U/ml) |
|---|---|---|---|
| Blank control group | 10 | 30.64 ± 11.18 | 20.84 ± 1.89 |
| Model group | 10 | 130.21 ± 11.39 | 47.84 ± 1.91 |
| Qiyeanshen Tablet | 10 | 78.13 ± 18.16** | 28.78 ± 3.75* |
| YXQN-1 (High) | 10 | 83.76 ± 17.94** | 45.19 ± 4.28** |
| YXQN-1 (Middle) | 10 | 96.10 ± 11.73*# | 47.3 ± 2.28*# |
| YXQN-1 (Low) | 10 | 107.72 ± 15.9*# | 49.31 ± 1.53*# |
| YXQN-2 (High) | 10 | 97.33 ± 16.23 | 48.22 ± 4.28 |
| YXQN-2 (middle) | 10 | 101.11 ± 19.01 | 50.2 ± 5.6 |
| YXQN-2 (Low) | 10 | 118.72 ± 18.75 | 55.5 ± 2.9 |

Compared with the model group, *P < 0.05, **P < 0.01; compared with YXQN-2, #P < 0.05.

3.4 Contents of 5-HT, 5-HIAA and DA

Compared with the model group, the contents of 5-HT, 5-HIAA and DA in rats in the high, middle and low dosage groups of YXQN-1 had statistical significance (P<0.05, P<0.01). The significant difference had not yet been found in each dosage group of the YXQN-2. In terms of 5-HT and 5-HIAA, compared with the equal dosage group of YXQN-2, the middle and low dosage groups of YXQN-1 had significant difference (P<0.05). In terms of DA, compared with the equal dosage group of YXQN-2, the middle and high dosage groups of YXQN-1 had significant difference (P<0.05). The results were shown in Table 6.

TABLE 6 effect of YXQN-1 and YXQN-2 on the contents of 5-HT, 5-HIAA and DA in rats ($\bar{x} \pm s$)

| Group | n | 5-HT (ng/g) | 5-HIAA (mg/d) | DA (ng/L) |
|---|---|---|---|---|
| Blank control group | 10 | 201.7 ± 7.8 | 125.23 ± 11.22 | 49.33 ± 10.51 |
| Model group | 10 | 126.6 ± 7.8 | 247.48 ± 1.10 | 65.16 ± 12.90 |
| Qiyeanshen Tablet | 10 | 185.3 ± 6.1* | 129.65 ± 3.10* | 54.04 ± 11.27 |
| YXQN-1 (High) | 10 | 185.2 ± 2.8* | 130.19 ± 24.28** | 56.01 ± 11.51*# |
| YXQN-1 (Middle) | 10 | 171.9 ± 3.3*# | 139.3 ± 22.28*# | 59.11 ± 10.85*# |
| YXQN-1 (Low) | 10 | 158.3 ± 4.6*# | 149.31 ± 1.53*# | 61.08 ± 10.51* |
| YXQN-2 (High) | 10 | 170.3 ± 6.3 | 158.22 ± 34.20 | 59.67 ± 10.32 |
| YXQN-2 (middle) | 10 | 145.1 ± 9.1 | 168.20 ± 25.60 | 61.28 ± 14.32 |
| YXQN-2 (Low) | 10 | 120.72 ± 8.5 | 155.5 ± 23.90 | 61.54 ± 15.20 |

4. Conclusion

Said pharmaceutical composition of present invention may ameliorate nitroglycerin-induced behavioral indices and biochemical indices in models of migraine rats. As shown in the research, said pharmaceutical composition of present invention is proven to have an effect on ameliorating nitroglycerin-induced behavioral indices in models of migraine rats, which is better than the comparison drug.

Pharmacodynamic Research 2. Effect of Pharmaceutical Composition (YXQN) on Change of Cerebral Blood Flow in Model of Migraine Rabbits 1. Materials 1.1 Commercially available 36 rabbits, weighing 2.2±0.5 kg, were randomly divided into 6 groups, 6 rabbits in each group. The animals were raised in laboratory of basic medicine college of Tianjin Medical University, under natural light with excellent ventilation and free access to water and food.

1.2 Drugs: tested drug was prepared by the method of Example 1 (YXQN-1), and comparison drug was prepared by the method of Chinese patent ZL200510073290.3 (YXQN-2). Both were provided by Tasly Pharmaceutical Co., Ltd.

1.3 Apparatus: ultrasound Doppler blood stream detector
2. Method
2.1 Grouping and Administration Animals were randomly divided into 6 groups according to body weight, 6 rabbits in each group: the model group; blank control group; high, and low dosage groups of YXQN-1 (0.782 g and 0.391 g extract/kg respectively); high and low dosage groups of YXQN-2 (0.782 g and 0.391 g extract/kg respectively). The model and blank control groups were administrated by gastric perfusion with equal volume of normal saline. Animal modeling method was the same as aforesaid Pharmacodynamic Research 1. Except treatment by drugs, the model group was administrated by ear vein injection of 5-HT (2 mg/kg) for consecutive 3 days, and at $3^{rd}$ day Diazepam injection (7.5 mg/rabbit) was added. Cerebral blood flow was assayed 30 min after the last administration. The rabbits were fixed in rabbit hutch. 2 MHz detector was used on the temporal to detect, with a sampling volume of 7 mm and a depth of 26±2 mm.

2. Statistical Management

All results were expressed as $\bar{x}\pm s$ and t-test was used between groups.

PI=2×(Vs−Vd)/(Vs+Vd)

PI: pulse index
Vs: blood flow velocity of contraction peak
Vd: blood flow velocity of diastole end
Vm: mean blood flow velocity 3. Results 3.1 Vs, Vd, Vm and PI Blood flow velocity in the blank control group remained unchanged. After modeling, the blood flow velocities in YXQN-1, YXQN-2 and model groups were decreased, having no statistical significance, as compared with the model group. After treatment, compared with the model group, the high and low dosage groups of YXQN-1 had statistical significance (P<0.05, P<0.01). The significant difference had not yet been found in each dosage group of the YXQN-2. Compared with the equal dosage group of YXQN-2, the high dosage group of YXQN-1 had significant difference (P<0.05). The results were shown in Table 7.

TABLET 7 effect of YXQN-1 and YXQN-2 on the change of cerebral blood flow in rabbits ($\bar{x} \pm s$)

| Group | n | Vs (cm/s) | Vd (cm/s) | Vm (cm/s) | PI |
|---|---|---|---|---|---|
| Blank control group | 6 | 43.53 ± 4.8 | 40.33 ± 3.22 | 41.56 ± 3.51 | 0.082 ± 0.001 |
| Model group | 6 | 24.71 ± 4.54 | 19.48 ± 3.10 | 21.16 ± 2.90 | 0.23 ± 0.03 |
| YXQN-1 (high) | 6 | 39.23 ± 5.84* | 34.34 ± 4.98** | 35.01 ± 4.23 | 0.22 ± 0.03 |
| YXQN-1 (low) | 6 | 38.33 ± 4.63*# | 33.76 ± 4.96*# | 34.08 ± 3.51 | 0.21 ± 0.03 |
| YXQN-2 (high) | 6 | 30.22 ± 4.31 | 28.13 ± 4.20 | 30.55 ± 5.32 | 0.23 ± 0.03 |
| YXQN-2 (low) | 6 | 29.18 ± 5.5 | 27.99 ± 4.90 | 27.34 ± 4.20 | 0.21 ± 0.03 |

4. Conclusion

Said pharmaceutical composition of present invention may ameliorate change of cerebral blood flow in model of migraine rabbits. As shown in this research, said pharmaceutical composition could improve the nitroglycerin-induced change of cerebral blood flow in migraine rabbits, which was better than the comparison drug.

What is claimed is:

1. A pharmaceutical composition for treatment of headache comprising 4-9 weight parts of *Radix Angelicae Sinensis*, 4-9 weight parts of *Rhizoma Chuanxiong*, 2-8 weight parts of *Radix Paeoniae alba*, 2-8 weight parts of *Radix Rehmanniae Preparata*, 10-15 weight parts of *Ramulus Uncariae cum Uncis*, 10-15 weight parts of *Caulis Spatholobi*, 10-15 weight parts of *Spica Prunellae*, 10-15 weight parts of *Semen Cassiae*, 10-15 weight parts of *Concha Margaritifera Usta*, 4-9 weight parts of *Rhizoma Corydalis* and 0.5-2 weight parts of *Herba Asari*, characterized in that said composition is prepared by a method as follows:
- a). preparation of #1 Extract: *Radix Angelicae Sinensis, Rhizoma Chuanxiong, Rhizoma Corydalis* and *Semen Cassiae* are mixed, extracted by using heating refluxing with ethanol, and filtered to remove impurities; and the ethanol is recovered and concentrated to give #1 Extract for later use;
- b). preparation of #2 Extract: *Radix Paeoniae alba* is extracted by using heating refluxing with ethanol, and filtered; and the ethanol is recovered and concentrated to give #2 Extract for later use;
- c). preparation of #3 Extract: *Radix Rehmanniae Preparata, Ramulus Uncariae cum Uncis, Caulis Spatholobi, Spica Prunellae, Concha Margaritifera Usta* and *Herba Asari* are mixed, decocted with water, filtered, concentrated, into which ethanol is added to leave it to stand still, and filtered; and the ethanol is recovered and concentrated to give #3 Extract for later use;
- d). preparation of formulations: aforesaid three Extracts are added with appropriate amount of excipients, dried, and granulated to obtain the final product.

2. The composition according to claim 1, characterized in that said composition is prepared by a method as follows:
- a). preparation of #1 Extract: *Radix Angelicae Sinensis, Rhizoma Chuanxiong, Rhizoma Corydalis* and *Semen Cassiae* are mixed, extracted by using heating refluxing with 3~6 fold of 50~80% ethanol for 2~3 times, the first time for 0.5~2.5 hours, the second and/or third time for 0.5~2 hours, and filtered to remove the impurities; and the ethanol is recovered and concentrated until the relative density is 1.250~1.350 at 70~80° C. to give #1 Extract for later use;
- b). preparation of #2 Extract: *Radix Paeoniae alba* is added with 3~6 fold of 50~80% ethanol, soaked, extracted by using heating refluxing for 2~3 times, the first time for 0.5~2.5 hours, the second and/or third time for 0.5~2 hours, and filtered; and the ethanol is recovered and concentrated until the relative density is 1.10~1.35 at 55~65° C. to give #2 Extract for later use;
- c). preparation of #3 Extract: *Radix Rehmanniae Preparata, Ramulus Uncariae cum Uncis, Caulis Spatholobi, Spica Prunellae, Concha Margaritifera Usta* and *Herba Asari* are combined, decocted with 4~10 fold of water for 2~3 times, the first time for 0.5~3 hours, the second and/or third time for 1~3 hours, filtered, concentrated until the relative density is 1.06~1.10 at 75~85° C., into which ethanol is added to make a final ethanol content of 60~85%, left to stand still for 12~24 hours, and filtered; and the ethanol is recovered and concentrated until the relative density is 1.270~1.350 at 75~85° C. to give #3 Extract for later use;
- d). preparation of formulations: aforesaid three Extracts are added with appropriate amount of excipients, dried, granulated to obtain the final product.

3. The composition according to claim 2, characterized in that said composition is prepared by a method as follows:
- a). preparation of #1 Extract: *Radix Angelicae Sinensis, Rhizoma Chuanxiong, Rhizoma Corydalis* and *Semen Cassiae* are mixed, extracted by using heating refluxing for 2 times with 4 fold of 70% ethanol, the first time for 2 hours and the second time for 1 hour, and filtered to remove the impurities; and the ethanol is recovered and concentrated until the relative density is 1.300~1.310 at 74~76° C. to give #1 Extract for later use;
- b). preparation of #2 Extract: *Radix Paeoniae alba* is added with 4 fold of 60% ethanol, soaked, extracted by using heating refluxing for 2 times, the first time for 2 hours and the second time for 1 hour, and filtered; and the ethanol is recovered and concentrated until the relative density is 1.23~1.33 at 65° C. to give #2 Extract for later use;
- c). preparation of #3 Extract: *Radix Rehmanniae Preparata, Ramulus Uncariae cum Uncis, Caulis Spatholobi, Spica Prunellae, Concha Margaritifera Usta* and *Herba Asari* are mixed, decocted for 2 times with 5 fold of water, the first time for 2 hours and the second time for 1 hour, filtered, concentrated until the relative density is 1.06~1.10 at 80° C., into which ethanol is added to make a final ethanol content of 65~70%, left to stand still for 12~24 hours, and filtered; and the ethanol is recovered and concentrated until the relative density is 1.320~1.325 at 79~81° C. to give #3 Extract for later use;
- d). preparation of formulations: aforesaid three Extracts are added with appropriate amount of excipients, dried, granulated to obtain the final product.

4. The composition according to claim 1, characterized in that said excipients in step d) include one or more kinds of filling agent and flavoring agent; said flavoring agent is selected from steviosin and aspartame.

5. The composition according to claim 4, characterized in that said filling agent is selected from dextrin, starch, soluble starch, sucrose, lactose and microcrystalline cellulose.

6. The composition according to claim 4, characterized in that said filling agent is dextrin and said flavoring agent is steviosin.

7. The composition according to claim 1, characterized in that the weight ratio of aforesaid three Extracts prepared by *Radix Angelicae Sinensis, Rhizoma Chuanxiong, Radix Paeoniae alba, Radix Rehmanniae Preparata, Ramulus Uncariae cum Uncis, Caulis Spatholobi, Spica Prunellae, Semen Cassiae, Concha Margaritifera Usta, Rhizoma Corydalis* and *Herba Asari* to the excipients is 40:60 to 65:35.

8. The composition according to claim 7, characterized in that the weight ratio of aforesaid three Extracts prepared by *Radix Angelicae Sinensis, Rhizoma Chuanxiong, Radix Paeoniae alba, Radix Rehmanniae Preparata, Ramulus Uncariae cum Uncis, Caulis Spatholobi, Spica Prunellae, Semen Cassiae, Concha Margaritifera Usta, Rhizoma Corydalis* and *Herba Asari* to the excipients is 55:45 to 65:35.

9. The composition according to claim 7, characterized in that said ratio of aforesaid three Extracts to the excipients is a ratio of dried extractum converted from aforesaid three Extracts to the excipients.

10. The composition according to claim 1, characterized in that, in step d), the formulation is prepared by fluidized-bed spray granulation method, comprising following steps: taking a part of filling agent, dissolving it with purified water, adding flavoring agent to dissolve by well-stirring to give slurry; adding well-prepared three Extracts into aforesaid slurry stepwise, stirring, adjusting density of the slurry, online filtering; putting the rest of filling agent into a granulator; performing spray granulation by adjusting granulating parameters; drying; granulating with a sieve; mixing totally and packaging to obtain the final product.

11. The composition according to claim 10, characterized in that addition amount of said flavoring agent accounts for 0~1% by weight of the total filling agent, and the weight ratio between the part of filling agent firstly added and the rest of the filling agent added later is 1:4 to 1.5:1.

12. A method for preparing the pharmaceutical composition of claim 1, characterized in that the method comprising following steps:
- a). preparation of #1 Extract: *Radix Angelicae Sinensis, Rhizoma Chuanxiong, Rhizoma Corydalis* and *Semen Cassiae* are mixed, extracted by using heating refluxing with ethanol, and filtered to remove impurities; and the ethanol is recovered and concentrated to give #1 Extract for later use;
- b). preparation of #2 Extract: *Radix Paeoniae alba* is extracted by using heating refluxing with ethanol, and filtered; and the ethanol is recovered and concentrated to give #2 Extract for later use;
- c). preparation of #3 Extract: *Radix Rehmanniae Preparata, Ramulus Uncariae cum Uncis, Caulis Spatholobi, Spica Prunellae, Concha Margaritifera Usta* and *Herba Asari* are mixed, decocted with water, filtered, concentrated, into which ethanol is added to leave it to stand still, and filtered; and the ethanol is recovered and concentrated to give #3 Extract for later use;
- d). preparation of formulations: taking a part of filling agent, dissolving it with purified water, adding flavoring agent to dissolve by well-stirring to give slurry; adding well-prepared three Extracts into aforesaid slurry stepwise, stirring, adjusting density of the slurry, online filtering; putting the rest of filling agent into a granulator; performing spray granulation by adjusting granulating parameters; drying; granulating with a sieve; mixing totally and packaging to obtain the final product.

13. A method for treating headache, traumatic cranial nerve syndrome, dizziness and vertigo, vexation and irritability, insomnia, or dreaminess, comprising administering a pharmaceutical composition of claim 1.

* * * * *